Nov. 11, 1969 L. K. WILEMAN Plant Pat. 2,937
NECTARINE TREE
Filed Oct. 23, 1967
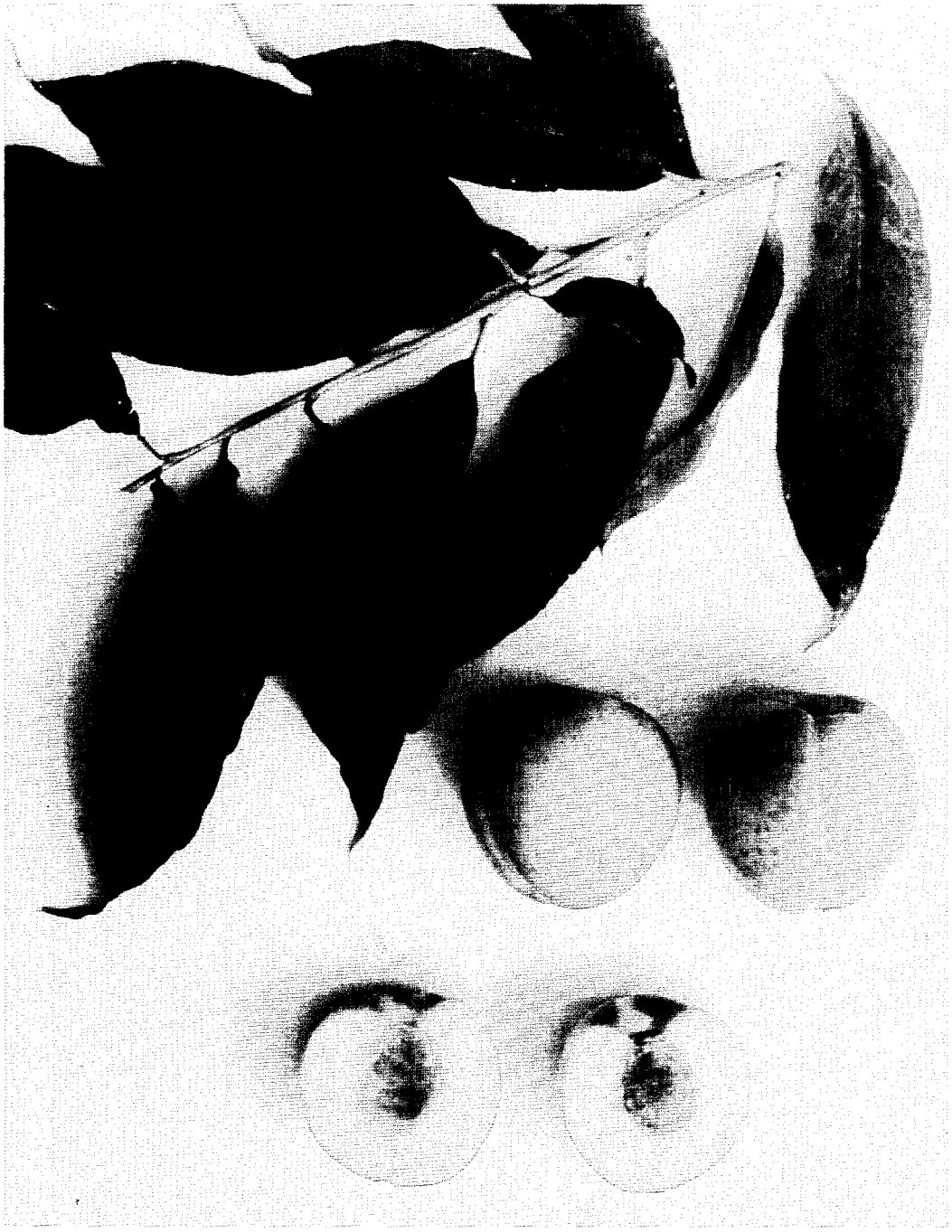
INVENTOR
Leonard K. Wileman
BY Webster & Webster
ATTORNEYS United States Patent Office Plant Pat. 2,937
Patented Nov. 11, 1969

2,937
NECTARINE TREE

Leonard K. Wileman, Cutler, Calif., assignor to Reedley Nursery, Inc., Reedley, Calif., a corporation of California Filed Oct. 23, 1967, Ser. No. 677,489
Int. Cl. A01h 5/08
U.S. Cl. Plt.—41 1 Claim

ABSTRACT OF THE DISCLOSURE

A nectarine tree generally similar to, and a mutation of, the Red Grand (United States Plant Patent No. 1,060); the essential distinction being in the period of ripening of the large, clingstone fruit having yellow flesh, and yellow skin substantially entirely overspread with red at maturity.

*Origin of the variety*

The herein claimed new and distinct variety of nectarine tree was found by me as a limb on one of the trees in my Red Grand orchard located near Cutler, Tulare County, Calif. I observed, after discovery of such limb, that is consistently bore good crops of fruit having an earlier ripening period than the fruit of the remainder of the tree and, in fact, throughout the entire Red Grand orchard.

Upon recognition by me of this distinctive characteristic of the above mutation limb, I determined to undertake asexual reproduction of the variety, with a view toward ultimate commercialization thereof.

*Asexual reproduction of the variety*

I successfully accomplished asexual reproduction of the present variety of nectarine tree by top-working on other trees in my orchard located as aforesaid. Under careful observation, it was determined that all such reproductions ran true in each and every respect to the parent; i.e. the original mutation limb.

*Summary of the variety*

The present variety of nectarine tree, saving and excepting the ripening period, carries forward—desirably—all of the general characteristics, in tree and fruit, of the Red Grand and which, in California, is one of the leading varieties of commercially grown nectarines.

The distinctive characteristic of the present variety is a ripening period which is approximately ten days earlier than the Red Grand grown under like conditions of soil and climate. Such earlier ripening period is of substantial advantage in that marketing of the generally Red Grand type of fruit can be initiated substantially earlier than at present.

In comparison to the Early Red Grand (United States Plant Patent No. 1,634), the fruit of the present variety is distinctively characterized—in addition to a ripening period which is approximately four days later—by a much more uniform ripening period, and a readily discernible much greater uniformity in the bright red overspreading color of the yellow-skinned fruit, in the smoothness of the surface thereof, and in the size of the fruit. As trees of the Early Red Grand variety have become older, the fruit borne thereby has not, and perceptively so, been of the evident quality—in the respects noted above—of the fruit of the present variety.

*Brief description of the drawing*

The drawing is an illustration, by photographic reproduction in color, of a twig with leaves, a detached leaf, and detached fruit; one fruit being cut in half to expose the flesh, and the stone remaining in one such half.

*Description of the variety*

The botanical details of this new and distinct variety of nectarine tree—with color definitions (except those in common color terms) referenced to Maerz and Paul Dictionary of Color—are as follows:

Tree:
- *Size.*—Large.
- *Vigor.*—Vigorous.
- *Growth.*—Spreading.
- *Production.*—Productive.
- *Bearing.*—Regular bearer.

Trunk:
- *Size.*—Stocky.

Branches:
- *Size.*—Stocky.

Lenticels:
- *Number.*—Medium.
- *Size.*—Medium.

Leaves:
- *Size.*—Large; length—6" to 7"; width—1¾" to 2".
- *Form.*—Lanceolate, acutely pointed.
- *Texture.*—Smooth.
- *Margin.*—Crenate.
- *Petiole.*—Medium length, medium thickness.
- *Glands.*—Average number, 4, medium, reniform, positioned usually 2 on petiole and 2 or more on margin of blade.
- *Color.*—Top side—Medium green (23–L–8), under side—Lighter green (22–K–5).

Flower buds:
- *Size.*—Medium.
- *Form.*—Plump.

Flowers:
- *Blooming period.*—About with Alberta (unpatented) peach, medium, as compared with other varieties.
- *Size.*—Large, showy.
- *Color.*—Pink.

Fruit:
- *Maturity when described.*—Hard ripe—July 20, 1967.
- *Date of first picking.*—July 10, 1967.
- *Date of last picking.*—July 20, 1967.
- *Size.*—Uniform, large, average diameter axially—3", average transversely in suture plane—3".
- *Form.*—Uniform globose.
- *Suture.*—Shallow, with slight depression beyond pistil point.
- *Ventral surface.*—Rounded.
- *Cavity.*—Rounded average depth—⅜", average breadth—¾", markings—usually completely covered with red.
- *Base.*—Flat.
- *Apex.*—Depressed.
- *Pistil point*—Lacking.

Skin:
- *Thickness.*—Thick.
- *Texture.*—Tough.
- *Tenacity.*—Tenacious to flesh.
- *Tendency to crack.*—None.
- *Pubescence.*—Lacking.
- *Color.*—Yellow (10–L–6) substantially completely overspread with red (5–L–4 to 6–L–4).

Flesh:
- *Amygdalin.*—Moderate.
- *Juice.*—Abundant.
- *Texture.*—Very firm when fruit well colored.
- *Ripens.*—Evenly.
- *Flavor.*—Subacid, delicate.

*Aroma.*—Distinct.
*Eating quality.*—Good to best.
*Color.*—Yellow (10–L–6). Surface of pit cavity—red (5–L–3), streaking lightly into flesh.

Stone:
*Type.*—Cling.
*Size.*—Large; average length—1 5/16", average breadth—1¼", average thickness—¾".
*Form.*—Oval to round.
*Base.*—Oblique.
*Hilum.*—Broad, oval.
*Apex.*—Rounded.
*Sides.*—Equal.
*Surface.*—Irregularly furrowed, pitted throughout.
*Ventral edge.*—Thick.
*Ridges.*—Continuous.
*Tendency to split.*—Slight.
*Color.*—Reddish brown (7–L–6 to 8–L–6).

Use: Market, local, dessert.
Keeping quality: Very good.
Shipping quality: Excellent.

The nectarine tree and its fruit herein described may vary in slight detail due to climatic and soil conditions under which the variety may be grown; the present description being of the variety as grown in the Central Valley of California.

I claim:

1. A new and distinct variety of nectarine tree, substantially as illustrated and described, which is generally similar in tree and fruit to the Red Grand and Early Red Grand, but is distinctively characterized, in comparison, by an intermediate ripening period which—under like conditions of soil and climate—is approximately ten days earlier than the Red Grand and approximately four days later than the Early Red Grand; and further characterized, in comparison to the Early Red Grand, by a much more uniform ripening period, and a much greater uniformity in the bright red overspreading color of the yellow-skinned fruit, in the smoothness of the skin, and in the size of the fruit.

References Cited

UNITED STATES PATENTS

P.P. 1,634 8/1957 Anderson ---------- Plants—41

ROBERT E. BAGWILL, Primary Examiner